(12) United States Patent
Leconte

(10) Patent No.: US 6,384,283 B1
(45) Date of Patent: May 7, 2002

(54) METHOD FOR PREPARING AMINONITRILE AND DIAMINE

(75) Inventor: Philippe Leconte, Meyzieu (FR)

(73) Assignee: Rhodia Fiber & Resin Intermediates, Courbevoie Cedex (FR)

( * ) Notice: Subject to any disclaimer, the term of this patent is extended or adjusted under 35 U.S.C. 154(b) by 0 days.

(21) Appl. No.: 09/674,551

(22) PCT Filed: May 11, 1999

(86) PCT No.: PCT/FR99/01127

§ 371 Date: Jan. 26, 2001

§ 102(e) Date: Jan. 26, 2001

(87) PCT Pub. No.: WO99/59962

PCT Pub. Date: Nov. 25, 1999

(30) Foreign Application Priority Data

May 15, 1998 (FR) .............................. 98 06426

(51) Int. Cl.⁷ .............................. C07C 209/48

(52) U.S. Cl. ...................... 564/492; 564/493

(58) Field of Search ................. 564/492, 493

(56) References Cited

FOREIGN PATENT DOCUMENTS

| FR | 2722709 A | 1/1996 |
|----|-----------|--------|
| WO | 9518090 A | 7/1995 |
| WO | 9618603 A | 6/1996 |
| WO | 9811060 A | 3/1998 |

*Primary Examiner*—Brian J. Davis
(74) *Attorney, Agent, or Firm*—Burns, Doane, Swecker & Mathis, L.L.P.

(57) ABSTRACT

The present invention relates to a process for the preparation of aminonitrile and of diamine by catalytic hydrogenation of dinitrile. It consists of a process for the preparation of aminonitrile and of diamine by catalytic hydrogenation of aliphatic dinitrile having from 3 to 12 carbon atoms, characterized in that the final reaction mixture, the catalyst of which has been separated beforehand, is acidified by addition of a sufficient amount of an inorganic or organic acid, before being subjected to an operation of distillation of the products of the reaction and of the unconverted dinitrile. It relates more particularly to the preparation of 6-aminocapronitrile and of hexamethylenediamine by hydrogenation of adiponitrile. The 6-aminocapronitrile can be hydrolysed in the liquid phase or in the gas phase to result in caprolactam. The hexamethylenediamine can be used very particularly to prepare polyamide-6,6 by reaction with adipic acid.

15 Claims, No Drawings

METHOD FOR PREPARING AMINONITRILE AND DIAMINE

This application is a 371 of PCT/FR99/01127 filed May 11, 1999.

The present invention relates to a process for the preparation of aminonitrile and of diamine by catalytic hydrogenation of dinitrile.

It relates more particularly to the preparation of 6-aminocapronitrile and of hexamethylenediamine by catalytic hydrogenation of adiponitrile.

The catalytic hydrogenation of an aliphatic dinitrile, in particular adiponitrile, to aminonitrile and diamine, in particular 6-aminocapronitrile and hexamethylenediamine, can be carried out, for example according to the teaching of Patent WO-A-96/18603, in the presence of a catalyst based on Raney nickel or on Raney cobalt, optionally comprising one or more promoter elements, and in the presence of a strong inorganic base, the hydrogenation being carried out in a medium comprising, in addition to the dinitrile, water, diamine and/or aminonitrile.

Reference may also be made to Patent EP-A-0,737,100, which discloses the hydrogenation of an aliphatic dinitrile, in particular adiponitrile, in the presence of a Raney nickel or cobalt doped chemically with one or more promoter elements and in the presence of a strong base, the hydrogenation being carried out in a medium comprising at least water and, if appropriate, an organic solvent, such as an alcohol or an amide.

Patent WO-A-97/10052 discloses the hydrogenation of nitrites, in particular adiponitrile, in the presence of a catalyst based on nickel or on cobalt at least partially in the reduced state, texturized by a phase comprising one or more doping metals in the form of oxides, and in the presence of a strong base, the hydrogenation being carried out in a medium comprising at least water and, if appropriate, an organic solvent, such as an alcohol or an amide.

In these processes of the prior art, the final reaction mixture is quantitatively analysed and the contents of possible impurities are determined. The said contents of impurities are generally low, indeed even zero.

However, it is very clearly necessary to carry out the separation of the constituents of the said reaction mixture, essentially water, the optional solvent, the other light compounds possibly present, the diamine and the aminonitrile formed, and the unconverted dinitrile.

The Applicant Company has observed that during the distillation of the reaction mixture, after separation of the catalyst by filtration, settling, centrifuging or any other means, significant and prohibitive amounts of by-products are formed, these by-products originating in particular from the decomposition of the dinitrile, in particular of adiponitrile. Without this being limiting, when the dinitrile employed is adiponitrile, the main one of these by-products is iminocyanocyclopentane (ICCP), with other heavier by-products.

The formation of by-products exhibits numerous disadvantages and it is consequently necessary to prevent it as far as possible. First of all, these by-products originate essentially from the conversion of the dinitrile, in particular adiponitrile, which results in a loss which cannot be ignored in industrial processes. Moreover, they result in colorations and/or they have a significant harmful influence on the level of the specifications which must be met, for example, both by hexamethylenediamine, for the preparation of polyamide-6,6, and by 6-aminocapronitrile, which results in caprolactam, itself the base material of polyamide-6.

In addition, these by-products are difficult to remove, which necessitates complex and expensive purification processes.

The object of the present invention is to overcome these significant disadvantages by reducing as far as possible the formation of such by-products during the distillation of the constituents of the reaction mixtures resulting from the catalytic hydrogenation of dinitriles, in particular of aliphatic dinitriles.

It consists of a process for the preparation of aminonitrile and of diamine by catalytic hydrogenation of aliphatic dinitrile having from 3 to 12 carbon atoms, optionally in the presence of a solvent, characterized in that the final reaction mixture, the catalyst of which has been separated beforehand, is acidified by addition of a sufficient amount of an inorganic or organic acid before being subjected to an operation of distillation of the products of the reaction and of the unconverted dinitrile.

Mention may more particularly be made, among dinitriles, of adiponitrile, methylglutaronitrile, ethylsuccinonitrile, dimethylsuccinonitrile, malononitrile, succinonitrile, glutaronitrile or dodecanedinitrile. Use may be made of mixtures of several dinitriles, in particular of mixtures comprising adiponitrile, methylglutaronitrile and ethylsuccinonitrile originating from the synthesis of adiponitrile from butadiene.

For convenience, the process of the invention will generally refer, in what follows, to adiponitrile and to its hydrogenation products, 6-aminocapronitrile and hexamethylenediamine, but it also applies to other dinitriles.

The process of the invention applies more particularly to the mixtures originating from the hydrogenation of dinitriles which is catalysed by at least one metal from group VIII of the Periodic Classification of the Elements as published in "Handbook of Chemistry and Physics, 51st edition (1970–1971)" by The Chemical Rubber Company.

More particularly, the hydrogenation of adiponitrile is carried out in a known way. The catalysts employed generally comprise at least one metal chosen from nickel, cobalt, iron, rhodium or ruthenium. These metals can be used in combination with one or more promoter elements. Mention may be made, as promoter elements, for example, of molybdenum, tungsten, titanium, chromium, iron, nickel, cobalt, copper, silver, gold, zinc, cadmium, lead, tin, palladium, platinum, osmium, rhenium, iridium, antimony, bismuth or rare earth metals.

The catalyst may or may not be deposited on a support. Use may be made, as supports, of alumina, silica, titanium dioxide, zirconium dioxide, magnesium oxide or active charcoals.

Preference is given, among non-supported catalysts, to Raney nickel and Raney cobalt, optionally comprising one or more promoter elements. Mention may be made, among the promoters more particularly suited to Raney nickel or to Raney cobalt, of titanium, molybdenum, tungsten, chromium, iron, zinc, copper, silver or gold.

Use may also be made of catalysts based on nickel or on cobalt at least partially in the reduced state, which metal is texturized by a phase comprising one or more doping metals (promoters) in the form of oxides, such as disclosed in Patent WO-A-97/10052.

Reference may be made, for the hydrogenation of adiponitrile in the presence of Raney nickel or of Raney cobalt, to, for example, Patents WO-A-96/18603, EP-A-0,737,100, EP-A-0,737,101 or EP-A-0,737,181.

The hydrogenation of adiponitrile, more particularly when it is carried out in the presence of Raney nickel, Raney cobalt, rhodium or ruthenium, is preferably carried out in the presence of a basic compound, such as an alkali metal or alkaline earth metal hydroxide.

The hydrogenation reaction is generally carried out in the presence of a solvent, such as water. In addition, the reaction can be carried out in the presence of an organic solvent, such as an alcohol or an amide, or of an inorganic solvent, such as liquid ammonia. The reaction mixture can also comprise, from the beginning of the reaction, variable amounts of products of the said reaction acting as solvents.

The solvent is separated from the reaction mixture, preferably after neutralization of the base present in the mixture, in particular when the base is an inorganic base.

The acid added to the reaction mixture after separation of the catalyst can be any inorganic acid, such as, for example, sulphuric acid, phosphoric acid, phosphorous acid, hydrochloric acid or nitric acid, or any organic acid, such as, for example, aliphatic, cycloaliphatic or aromatic carboxylic acids, which can be mono- or polyfunctional, or aliphatic, cycloaliphatic or aromatic sulphonic acids. Mention may be made, as non-limiting examples of organic acids, of acetic acid, propionic acid, valeric acid, hexanoic acid, adipic acid, terephthalic acid, glutaric acid, succinic acid, methylglutaric acid, ethylsuccinic acid, para-toluenesulphonic acid, methanesulphonic acid or fluoromethanesulphonic acid. Use may also be made of acidic resins, in particular resins comprising sulpho groups.

The amount of acid employed must generally be such that it corresponds at least to stoichiometry with respect to the basic inorganic compounds present in the reaction mixture resulting from the hydrogenation of the dinitrile, more particularly of adiponitrile. The addition is generally carried out of 0.0005% to 2% by weight of acid with respect to the weight of the reaction mixture and preferably of 0.001% to 1% as weight by weight.

When the acid used is an acidic resin, the ratio by weight has hardly any meaning. The reaction mixture to be treated can either be passed over the said resin or, if appropriate, resin can be introduced into the mixture before it is distilled.

After the addition of acid, the reaction mixture is distilled in order to separate the solvent and the other light compounds which it may comprise, the hexamethylenediamine and the 6-aminocapronitrile formed, and the unconverted adiponitrile which it comprises and which can be recycled in a fresh hydrogenation. The hexamethylenediamine and the 6-aminocapronitrile can be distilled successively in two columns or, in a first step, can be distilled together in order to heat the unconverted adiponitrile for a shorter period of time. In the second alternative form, the hexamethylenediamine and the 6-aminocapronitrile are subsequently separated from one another by distillation. The adiponitrile can be recycled directly in a hydrogenation operation or can be itself distilled beforehand in order to remove the heavy products which it may comprise, in particular the salts formed by the acid added. The 6-aminocapronitrile can be hydrolysed in the liquid phase or in the gas phase in order to result in caprolactam. This hydrolysis is carried out according to known techniques, in the presence or absence of a catalyst and optionally after an additional purification of the 6-aminocapronitrile. The caprolactam results by polymerization in polyamide-6. The hexamethylenediamine can be used very particularly to prepare polyamide-6,6 by reaction with adipic acid.

When the light compounds have been separated, the distillation is generally carried out under a pressure of less than atmospheric pressure.

The amount of by-products formed during the distillation is greatly reduced in comparison with a distillation carried out without prior addition of acid or with addition of acid carried out after separation of the 6-aminocapronitrile and the hexamethylenediamine. The examples which follow illustrate the invention.

EXAMPLE 1

Adiponitrile is hydrogenated continuously at 50° C. under 20 bar of hydrogen in the presence of 15% by weight with respect to the reaction mixture of Raney nickel (comprising 1.8% by weight of Cr with respect to the Ni) and of potassium hydroxide in a ratio of approximately 0.42% by weight with respect to the reaction mixture.

The reaction mixture has the following composition by weight: 27% of hexamethylenediamine (HMD), 38% of 6-aminocapronitrile (ACN), 25% of adiponitrile (AdN) and 9% of water and it additionally comprises 0.0080% of potassium hydroxide.

The presence of iminocyanocyclopentane (ICCP) is not detected by quantitative analysis by gas chromatography.

63 mg of orthophosphoric acid are added to 450 g of this mixture (approximately 1 mol per mole of potassium hydroxide).

The water is subsequently distilled off at atmospheric pressure over 1 h.

The combined HMD/ACN is subsequently distilled off under reduced pressure over 2 h until a temperature in the boiler of 185° C. is reached.

The ICCP is then quantitatively analysed on a sample of the distillation bottoms (AdN): 0.003% of ICCP is found.

In order to simulate a continuous operation during which the distillation bottoms have a longer residence time, the said distillation bottoms are maintained for a further 2 h at 185° C.

Quantitative analysis of ICCP is carried out on the distillation bottoms thus treated: 0.010% of ICCP is then found.

COMPARATIVE TEST 1

This comparative test is carried out on 450 g of the mixture prepared by hydrogenation of AdN in the first part of Example 1.

The water is subsequently distilled off at atmospheric pressure over 1 h.

The combined HMD/ACN is subsequently distilled off under reduced pressure over 2 h until a temperature in the boiler of 185° C. is reached.

The ICCP is then quantitatively analysed on a sample of the distillation bottoms (AdN): 12% of ICCP is found and it is found that 23% of the AdN present in the starting mixture has disappeared: conversion into ICCP, on the one hand, and into heavy products (boiling point greater than that of AdN), on the other hand.

In the absence of treatment with an acid before the distillation of the constituents of the mixture, the formation of far more ICCP is therefore observed than in the context of the invention with, in addition, the appearance of very large amounts of heavy products which have no economic value, at the expense of the AdN present in the starting mixture. 63 mg of orthophosphoric acid (same amount as in Example 1) are added to the preceding distillation residue.

The AdN is then distilled off under reduced pressure over 1 h.

The amount of ICCP and of heavy compounds remaining in the boiler is substantially the same as the amount quantitatively analysed before addition of the phosphoric acid.

What is claimed is:

1. A process for the preparation of aminonitrile and diamine comprising conducting catalytic hydrogenation of aliphatic dinitrile having from 3 to 12 carbon atoms, optionally in the presence of a solvent, separating the catalyst from the reaction mixture, acidifying the reaction mixture by addition of a sufficient amount of an inorganic or organic acid, and extracting, by distillation, the products of the reaction and the unconverted dinitrile.

2. The process according to claim 1, wherein the catalyst comprises at least one metal from group VIII of the Periodic Classification of the Elements.

3. The process according to claim 1, wherein the reaction mixtures originate from the preparation of 6-aminocapronitrile and of hexamethylenediamine by catalytic hydrogenation of adiponitrile.

4. The process according to claim 1, wherein the hydrogenation is carried out in the presence of catalysts comprising nickel, cobalt, iron, rhodium, ruthenium, or mixtures thereof, optionally in combination with one or more promoter elements.

5. The process according to claim 4, wherein the promoter elements are selected from the group consisting of molybdenum, tungsten, titanium, chromium, iron, nickel, cobalt, copper, silver, gold, zinc, cadmium, lead, tin, palladium, platinum, osmium, rhenium, iridium, antimony, bismuth and rare earth metals.

6. The process according to claim 1, wherein the catalyst is deposited on a support selected from the group consisting of alumina, silica, titanium dioxide, zirconium dioxide, magnesium oxide and active charcoals.

7. The process according to claim 1, wherein the catalyst is selected from Raney nickel and Raney cobalt, optionally comprising one or more promoter elements comprising titanium, molybdenum, chromium, iron, tungsten, zinc, copper, silver or gold.

8. The process according to claim 1, wherein the catalyst is selected from the group consisting of catalysts based on nickel or on cobalt at least partially in the reduced state, which metal is texturized by a phase comprising one or more promoter metals in the form of oxides.

9. The process according to claim 1, wherein the acid added to the reaction mixture after separation of the catalyst is an inorganic acid or an organic acid.

10. The process according to claim 1, wherein the amount of acid employed is approximately stoichiometrically equivalent to the basic inorganic compounds present in the reaction mixture resulting from the hydrogenation of the dinitrile.

11. The process according to claim 1, wherein the amount of acid employed represents from 0.0005% to 2% by weight of acid with respect to the weight of the reaction mixture.

12. The process according to claim 1, wherein the solvent can be separated from the reaction mixture before or after addition of the acid.

13. The process according to claim 9, wherein the inorganic acid comprises sulphuric acid, phosphoric acid, phosphorous acid, hydrochloric acid or nitric acid.

14. The process according to claim 9, wherein the organic acid comprises aliphatic, cycloaliphatic or aromatic carboxylic oxides which can be mono or polyfunctional, or aliphatic, cycloaliphatic or aromatic sulphonic acid or an acidic resin.

15. The process according to claim 11, wherein the amount of acid employed represents from 0.001% to 1% as weight by weight.

* * * * *